United States Patent [19]

Antonissen et al.

[11] Patent Number: 5,136,906
[45] Date of Patent: Aug. 11, 1992

[54] SLICING MACHINE

[75] Inventors: Peter Antonissen; Hugh M. Arthur, both of Norwich, England

[73] Assignee: Thurne Engineering Co., Ltd., England

[21] Appl. No.: 675,821

[22] Filed: Mar. 27, 1991

[30] Foreign Application Priority Data

Mar. 27, 1990 [GB] United Kingdom ............... 9006803

[51] Int. Cl.⁵ .............................................. B26D 5/20
[52] U.S. Cl. ........................................ 83/42; 83/363; 83/365; 83/367; 83/932; 382/8
[58] Field of Search ............... 83/75.5, 361, 365, 371, 83/932, 76.2, 76, 363, 364, 13, 42, 367; 382/1, 8; 364/474.12

[56] References Cited

U.S. PATENT DOCUMENTS

| | | | |
|---|---|---|---|
| 2,954,811 | 10/1960 | Hensgen et al. | 83/367 |
| 3,133,571 | 5/1964 | Hensgen et al. | 83/364 |
| 4,114,492 | 9/1978 | Skidmore | 83/371 |
| 4,532,840 | 8/1985 | Antonissen | 83/75.5 X |
| 4,598,618 | 7/1986 | Kuchler | 83/365 X |
| 4,776,023 | 10/1988 | Hamada et al. | 382/8 |
| 5,054,345 | 10/1991 | Weber | 83/365 |

FOREIGN PATENT DOCUMENTS 8706145 12/1987 Fed. Rep. of Germany .
2496269 6/1982 France .

OTHER PUBLICATIONS

European Search Report.

Primary Examiner—Frank T. Yost
Assistant Examiner—Kenneth E. Peterson
Attorney, Agent, or Firm—Sughrue, Mion, Zinn, Macpeak & Seas

[57] ABSTRACT

A slicing machine for cutting slices from a product includes a camera (6) which views a cut face (5) of the product. A boundary recognition processor (14) processes image signals from the camera (6) to determine a boundary of the cut face (5). A parameter characteristic of the cut face (5) is calculated from image data corresponding to regions of the cut face within the determined boundary. A control signal generating circuit generates a control signal to control the operation of the slicer in accordance with the determined parameter.

In a preferred example, the boundary is analysed to determine the location of any secondary regions (10) of the cut face (5) and the characteristic parameter is calculated from image data corresponding to regions of the cut face other than the secondary regions.

11 Claims, 4 Drawing Sheets

SLICING MACHINE

BACKGROUND OF THE INVENTION

The present invention relates to a slicing machine. Such machines are principally, but not exclusively, used for slicing food products, particularly slicing cheese, meat and pressed or moulded meat products.

Typically such a slicing machine includes a rotating blade and means to feed the product forward towards the blade so that successive slices are cut from one face of the product. The distance through which the product is advanced between successive cuts of the blade determines the thickness of the slices. Where the product is of uniform shape and density then it may be sufficient to use a single predetermined slice thickness to give a slice or group of slices of the required weight. In general however variations in the shape and density of the product mean that the weight of a slice of a given thickness varies. A previous approach to dealing with this variation is described and claimed in the applicants' earlier patent EP-B-0,127,463. This patent describes and claims a process in which an automatic slicing machine is programmed to vary the thickness of the slices in accordance with a typical weight distribution for the product. Although this system achieves good results where the product shape or envelope varies in a predictable manner it still tends to produce a number of slices which are outside the required weight range when the actual weight density distribution departs from the expected distribution.

It has also been proposed to make some determination of the cross-sectional area of the product as it is cut. This may be done, for example, by placing a light source and a photodetector array in front of the cut face of the product. The area of the array which is illuminated by the "image" of the cut face is then used as an indication of the cross-sectional area. Although such a system is better able to cope with variations in the shape of the product it still tends to produce slices which are off-weight when there is variation in the density of the product, or when there is fragmentation of the product.

SUMMARY OF THE INVENTION

According to the present invention, a slicing machine for cutting slices from a product includes a camera arranged to view a cut face of the product, boundary recognition means arranged to process image signals from the camera to determine a boundary of the cut face, calculating means arranged to calculate a parameter characteristic of the cut face from image data corresponding to regions of the cut face within the boundary, and control signal generating means, arranged to generate a control signal to control the operation of the slicer in accordance with the determined parameter.

It is found that by processing an image output by a camera to determine the boundary of the face and subsequently carrying out further processing on the image data within the boundary, parameters such as the area or density of the face can be determined with far greater accuracy than has hitherto been possible. Eliminating data outside the boundary results in a significant increase in the efficiency of subsequent image processing steps.

Preferably the apparatus further comprises boundary analysis means arranged to determine from the boundary the location of any secondary regions of the cut face, and the calculating means are arranged to calculate the parameter from image data corresponding to regions other than secondary regions.

By a "secondary region" is meant a feature such as an island distinct from the main region of the cut face but abutting or joined to that main region in the plane of the cut by a neck or similar feature. Such secondary regions may be formed by pieces of detached meat appearing within the vision frame of the camera as well as by islands which although initially integral with the slice in the plane of the cut would tend subsequently to become detached from the slice. The present invention by excluding such secondary regions from the calculation of the control parameter eliminates the gross errors which otherwise occur in the presence of such secondary regions.

The location and area of the cut face may be determined solely from the boundary. Alternatively tactile sensing means may be used to determine the position of an edge of the cut face relative to one or more fixed shear-edges. The boundary analysis means may then be arranged in determining the location of any secondary regions to compare the shape and location of the boundary along the edge with the location of the edge as indicated by the tactile sensing means.

Preferably the boundary analysis means are arranged to identify any opposing non-contiguous parts of the boundary, to determine the distance between the said parts of the boundary, and to compare that distance with a predetermined threshold. Preferably the image processing means are arranged to recognise sub-regions of the face having different characteristic densities and to determine from the total areas of the respective sub-regions the mean density of the face.

According to a further aspect of the present invention, a method of controlling a slicing machine includes viewing with a camera a region including a cut face of the product, processing image signals from the camera to determine a boundary of the cut face, calculating a parameter characteristic of the cut face from image data corresponding to regions of the cut face within the boundary, and generating a control signal to control the operation of the slicer in accordance with the determined parameter.

Preferably the method further comprises analysing the boundary to determine the location of any secondary regions, and the parameter is calculated from image data corresponding to regions other than secondary regions.

Preferably the method further comprises recognising sub-regions of the face defined by the boundary having different characteristic densities and calculating from the respective areas of the different sub-regions the mean density of the face.

Preferably the method includes identifying any opposing non-contiguous parts of the boundary, determining the distance between the said parts of the boundary, and when that distance falls below a predetermined threshold extending the boundary to join the non-contiguous opposing parts and to exclude the secondary region. Preferably the method includes determining the length of the boundary between the two said non-contiguous opposing parts and only extending the boundary to exclude the secondary region when the length of the boundary between the two parts exceeds a predetermined threshold.

BRIEF DESCRIPTION OF THE DRAWINGS

A system in accordance with the present invention will now be described in detail with reference to the accompanying drawings in which.

EMBODIMENT

Figure 1:
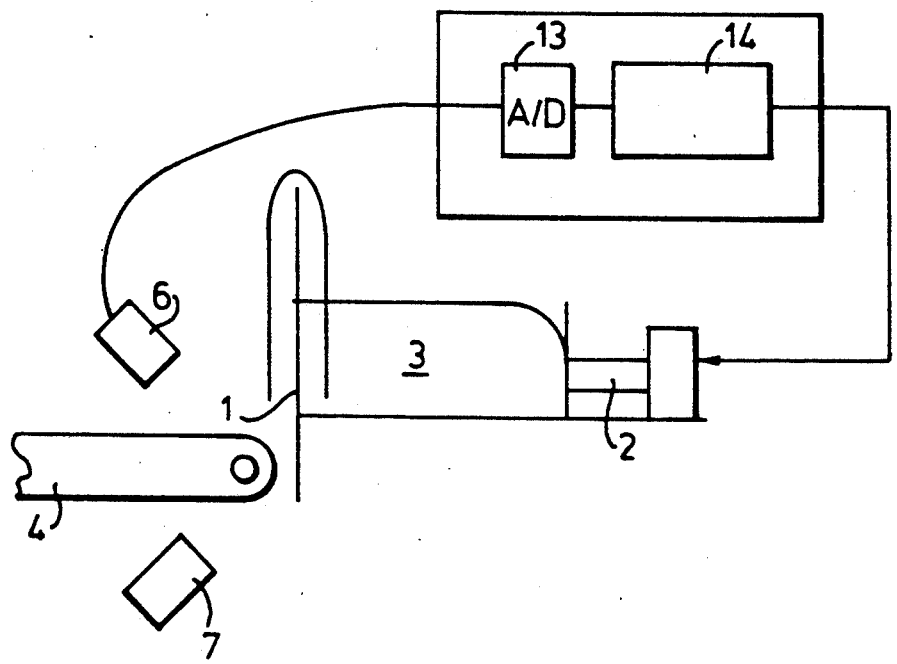
FIG. 1 is a side elevation of the system.

A slicing machine includes a slicing blade 1 and a feed mechanism 2 arranged to push a product 3 towards the slicer 1. Slices cut from the end-face 5 of the product 3 fall onto a conveyor 4. A source of illumination 7 is provided to one side of the end-face 5 of the product 3. The output from the camera 6 is taken to image-processing hardware which operates as described in further detail below to generate an appropriate control parameter for the slicer.

The first step in processing the image output by the camera 6 is to distinguish the background of the cut-face from the face itself. In general, the background is darker than the face and so can be distinguished by comparing the intensity of the pixels in the image field with an appropriate threshold. The manner in which the appropriate threshold is selected is described in greater detail in our co-pending application, title "Slicing Machine", agents reference 80/3553/04, claiming priority from British application number 9006304.0.

The camera 6 is set so that the lower edge of the field of view coincides with the bed shear-edge 8, so that when the product is held against a vertical shear-edge guide 9 the view of the camera encompasses the product on two sides at right-angles to each other. The product is illuminated from below, so that the area within the frame but beyond the product periphery appears much darker than the product face, irrespective of the strength of the illumination source. The camera scan is initiated from a pulse from the slicer blade at the point where the field of view is clear of the blade. The camera 6 may be of any known type with or without distinguishing colour facilities, but will preferably use a CCD to ensure rapid capture of the frame. The captured frame is immediately transferred using known frame-grabber techniques and converted into a digital grid by A/D conversion 13 for further computation within the image-processing hardware 14. The camera is simultaneously cleared for the next frame.

Figure 4:
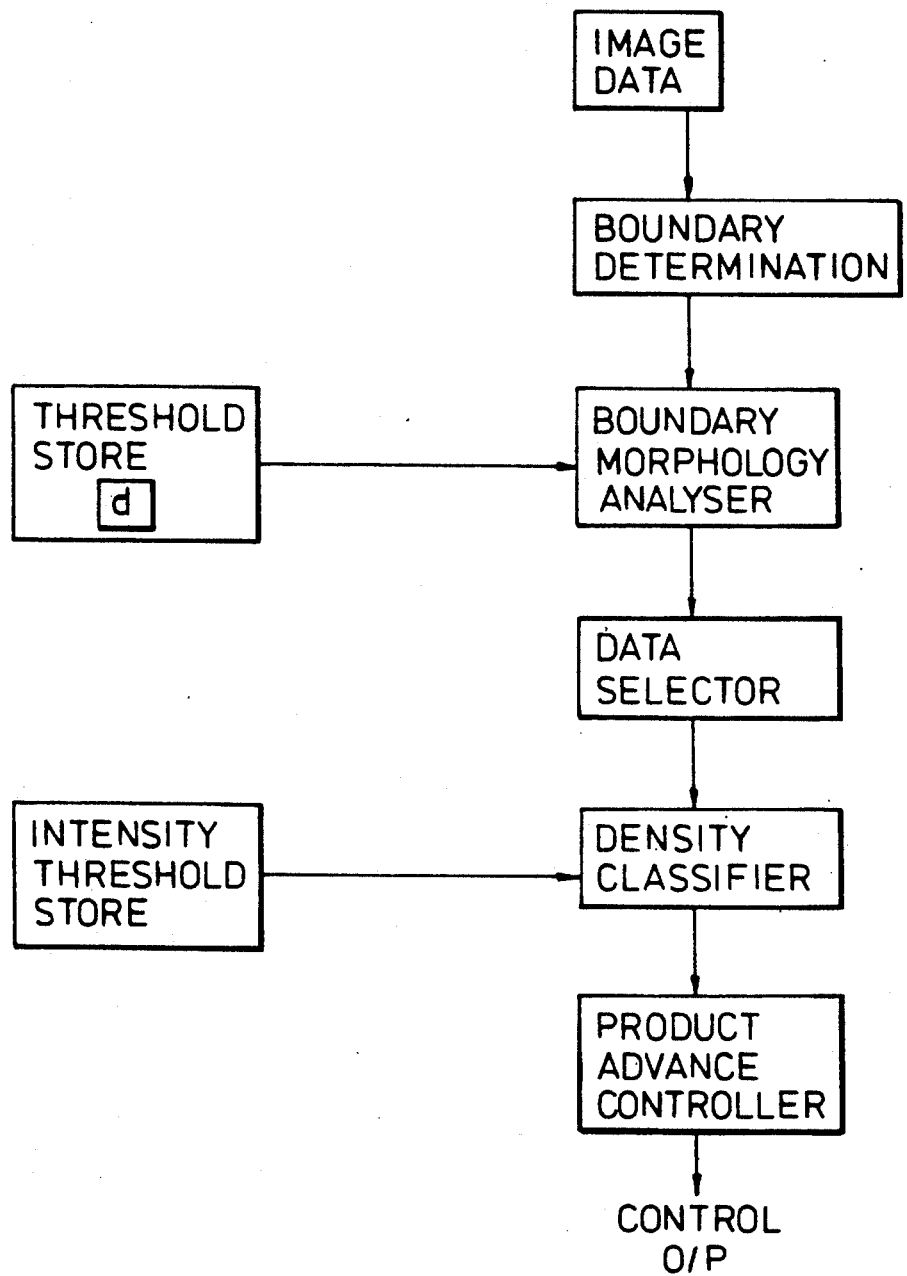
FIG. 4 is a block diagram.

The image processing is illustrated in FIG. 4. Having first eliminated from the data those pixels which fall below a certain intensity threshold and so are judged to form part of the background, the remaining pixels are processed to determine, amongst other features, the location of the boundary. This may be done using one of a number of conventional edge-tracing techniques, such as, for example, chain coding. Such techniques are described in standard texts such as "Digital Image Processing" by Gonzales and Wintz, published by Addison Wesley. Then from the characteristics of the boundary the location of any secondary regions is determined and such regions eliminated from the data before further processing is carried out.

Some meat fragmentation is unavoidable in any slicing process. Accordingly, occasional pieces of detached meat 10 will appear within the vision frame of the camera and may remain there for a number of cycles. Fat build-up 11 will also occur, particularly along the vertical shear-edge and can remain there for a long time, i.e. many slicing cycles.

The inclusion of these extraneous components in the product area calculations would completely invalidate the slice thickness calculations and must be removed.

Various methods may be used based on known morphological methods. Firstly, to eliminate any separate islands, the different boundaries defining complete contours are identified and the contour of interest selected. In our case, this would be the largest contour represented by the advancing meat since all other contours would be those of the smaller observed areas, that is the fragments.

However, this would not cover the situation where a fragment contacts the meat and, although not connected with it appears to be so.

The resolution to this problem could be an extension of the contour morphological method described above, whereby the whole or part of the largest contour is checked to determine if the envelope features a narrow neck with an appended area, suggesting a peninsula.

In this instance, the decision as to whether the peninsula area should be included in the total area for computing purposes, may be based on the ratio of the periphery of the peninsula between the two closest points at the neck versus the distance between these two points.

The choice of ratio can provide a high probability for the correct decision to be arrived at, but requires a considerable degree of computing power.

Figure 2A:
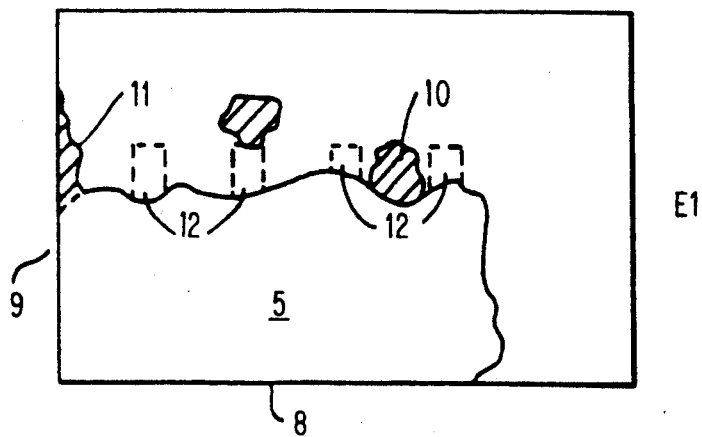
FIGS. 2a to 2c show the field view of the camera of FIG. 1.

A preferred resolution of the fragment elimination problem is illustrated in FIG. 2. FIG. 2a is the image of the product face 5, bounded by the horizontal and vertical shear-edges 8, 9 with hold down fingers 12 pressing on the top surface.

The hatched areas represent scraps of meat (lean and fat) on and between hold down fingers 12 and (substantially fat) adhering onto the vertical shear-edge. The contour adapting motion of the hold down fingers 12 is usually vertical and the width of these fingers is known, as is also their disposition relative to the vertical shear-edge 9 and may be held in a look-up table, either via operator entry, but preferably via a sub-routine using a vision system sub-routine at start up according to known art.

The fingers themselves are either made from very dark material or so coated and are shown for illustration purposes only, and would not normally appear in this view.

Figure 2B:
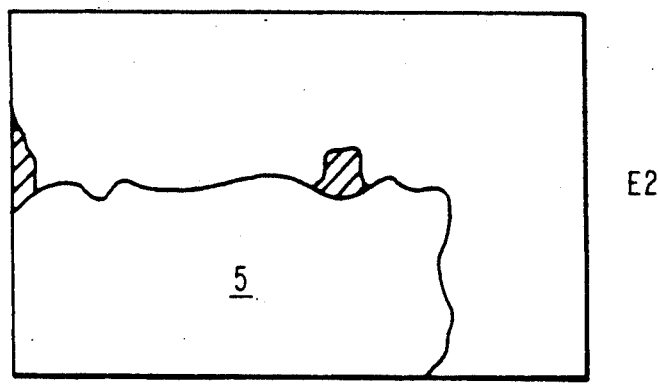

The final enhanced virtual image is now re-processed as follows. The clearly separated islands, representing islands of scrap, having been removed from the virtual image, as shown in FIG. 2b and explained above, the product boundary along the top edge of the virtual image is inspected and where substantial protrusions occur either side of any of the fingers, these protrusions are removed from the virtual image and hence from all subsequent computations.

The computation as to whether a protrusion between the fingers is likely to be attached or not uses techniques such as a measure of the highest point on the virtual profile relative to the mean height at the opposing heights of the fingers or, alternatively the ratio of the profile perimeter between adjacent fingers relative to the distance between them, compared to pre-entered criteria values.

Figure 2C:
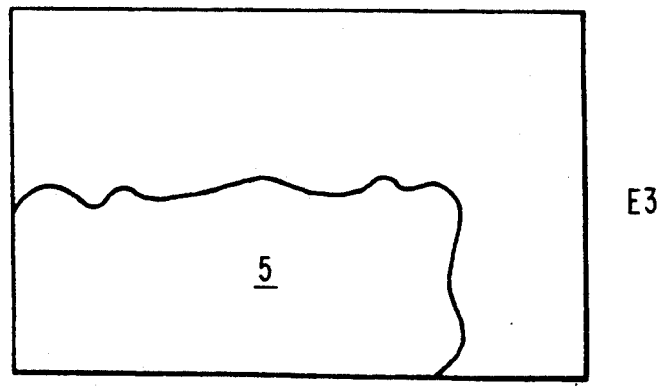

The product boundary along the top edge situated between the vertical shear-edge and the first hold down finger and the product boundary beyond the last hold down finger may be similarly inspected employing any of the techniques described above, thus leaving only the face of the advancing product face in the frame, as shown in FIG. 2c. Once the extraneous regions have been eliminated from the image data it is subject to further processing to calculate both the total area of the face and the relative areas of fat and lean. As described in further detail in the above cited co-pending application, the different areas are distinguished on the basis of different pixel intensities. The overall density of the face is then calculated in accordance with the proportions of fat and lean and an appropriate slice thickness determined. A control signal is output to the slicer to produce the required slice thickness.

Figure 3A:
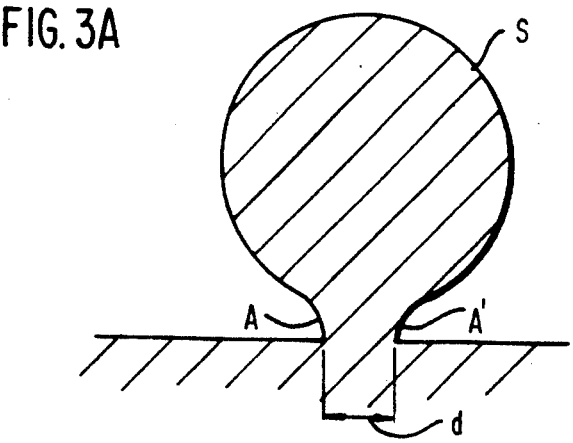
FIGS. 3a to 3c are diagrams showing the elimination of a secondary region.
Figure 3B:
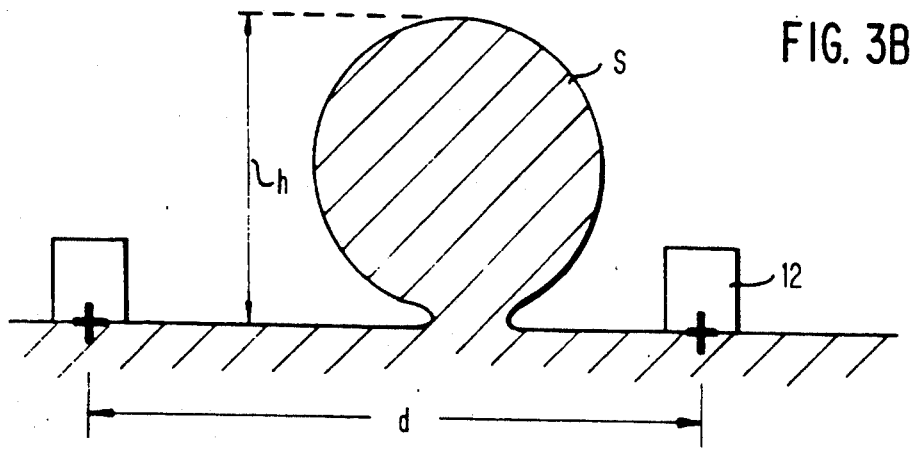
Figure 3C:
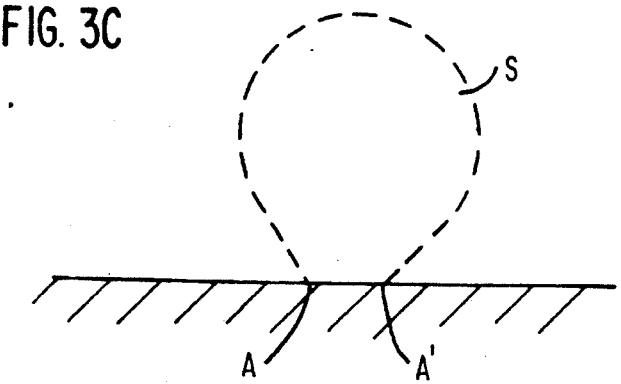

FIG. 3a illustrates one possible form of the computation for testing and eliminating the secondary regions. Opposing non-contiguous regions A, A' are identified by morphological analysis of the boundary. These regions define the throat of a secondary island. The distance d between these regions and the length S of the boundary between the regions are calculated and compared with a predetermined parameter. If the ratio of S to d exceeds this predetermined parameter then the region is a secondary region and is eliminated from subsequent calculations by effectively joining A directly to A' as shown in FIG. 3c. Alternatively as shown in FIG. 3b, the calculation may be related to the positions BB' of two of the hold down fingers 12 and may include a calculation based on the extent h of the region above the level of the fingers 12.

We claim:

1. A control system for a slicing machine for cutting slices from a workpiece, said control system comprising:
   means for viewing a cut face of said workpiece and outputting two-dimensional image data;
   a processor responsive to said image data output by said means for viewing for calculating a parameter characteristic of said cut face; and
   means for generating a control signal operatively connected to said processor and arranged to output a control signal for controlling said slicing machine in dependence on said parameter;
   said processor comprising means for determining, from said image data, a boundary of said cut face and means for selecting said image data corresponding to regions of the cut face within said boundary and calculating therefrom said parameter, wherein said processor further comprises means for analyzing said boundary and determining therefrom a location of any secondary regions of the cut face, said means for selecting being arranged to calculate said parameter from said image data corresponding to regions of said cut face other than said secondary regions.

2. The system of claim 1, further comprising tactile sensing means for determining a position of an edge of said cut face relative to one or more fixed shear edges.

3. The system of claim 1, wherein said means for analysing said boundary include means for identifying any opposing non-contiguous segments of said boundary, said means for analysing determining a distance between said segments of said boundary and comparing said distance with a predetermined threshold.

4. The system of claim 1, wherein said processor includes means for recognising sub-regions of said face having different characteristic densities and calculating from a total area of each of said respective sub-regions a mean density of said face.

5. A slicing machine for cutting slices from a workpiece comprising a slicing blade, means for advancing said workpiece towards said slicing blade, and means operatively connected to said means for advancing for controlling a distance by which said workpiece is advanced between successive slices, thereby determining a slice thickness;
   wherein said means for controlling comprise:
   means for viewing a cut face of said workpiece and outputting two-dimensional image data;
   a processor responsive to said image data output by said means for viewing for calculating a parameter characteristic of said cut face; and
   means for generating a control signal operatively connected to said processor and arranged to output a control signal for controlling said slicing machine in dependence on said parameter;
   said processor comprising means for determining, from said image data, a boundary of said cut face and means for selecting said image data corresponding to regions of the cut face within said boundary and calculating therefrom said parameter, wherein said processor further comprises means for analyzing said boundary and determining therefrom a location of any secondary regions of the cut face, said means for selecting being arranged to calculate said parameter from said image data corresponding to regions of said cut face other than said secondary regions.

6. The machine of claim 5, wherein said image processing means are arranged to recognise sub-regions of said face having different characteristics densities and to determine from a total area of each of the respective sub-regions a mean density of the face as said characteristic parameter, the control signal varying said slice thickness in dependence on said parameter thereby producing a desired slice weight.

7. A method of controlling a slicing machine for cutting slices from a workpiece comprising:
   viewing a region including a cut face from said image data corresponding to regions of said face within said boundary;
   generating a control signal for controlling operation of said slicing machine in accordance with said characteristic parameter; and
   analyzing said boundary and determining therefrom a location of any secondary regions of said cut face, and calculating said characteristic parameter from said image data corresponding to regions of said cut face other than said secondary regions.

8. The method of claim 7, further comprising recognising sub-regions of said face defined by said boundary having different characteristic densities, and calculating from respective areas of said sub-regions a mean density of said face.

9. The method of claim 7, wherein said step of analysing said boundary includes identifying any opposing non-contiguous segments of said boundary, determining a distance between said segments, and, when said distance falls below a predetermined threshold, extending image data representing said boundary thereby joining said non-contiguous opposing parts and excluding said secondary region.

10. The method of claim 9, wherein said image data corresponding to said non-contiguous opposing segments is extended only when a length of said boundary between said segments is determined to exceed the predetermined threshold.

11. The method of claim 9 wherein said parameter is a function of density of said cut face of said workpiece and said control signal varies thickness of slices cut by said slicing machine thereby producing a desire slice weight.

* * * * *